April 2, 1957 M. M. SMITH Plant Pat. 1,586
ORNAMENTAL PLUM TREE
Filed May 9, 1955 2 Sheets-Sheet 1
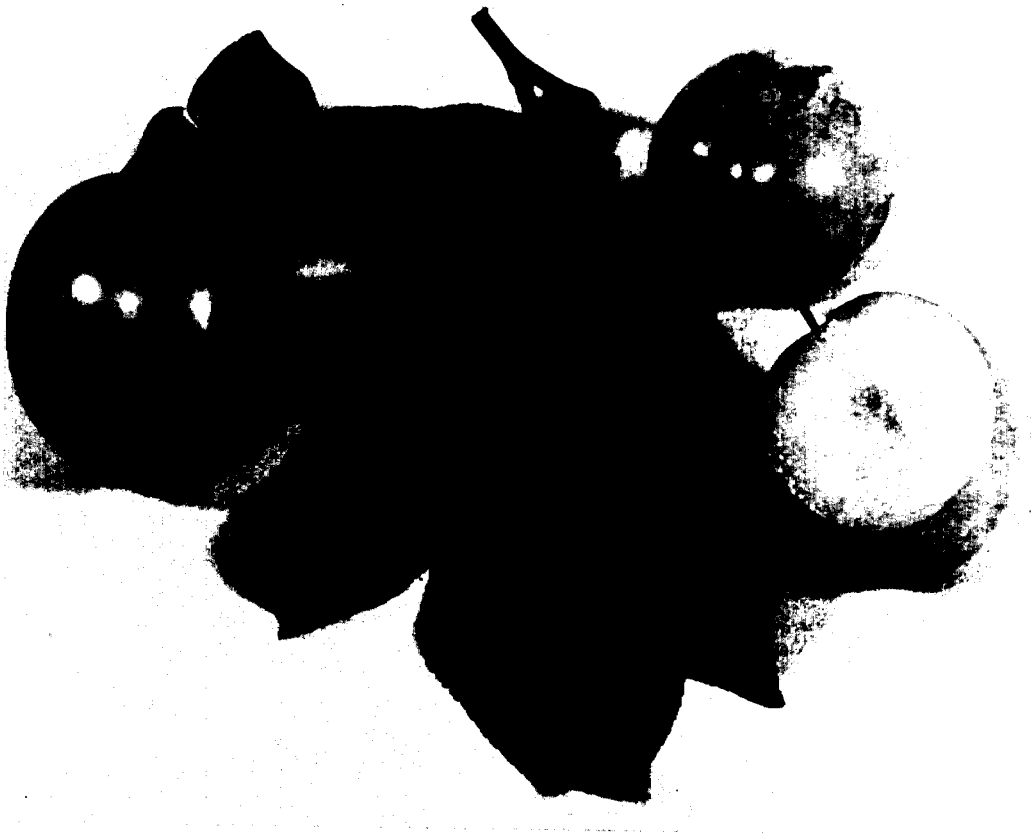
INVENTOR
MILDRED M. SMITH
BY F. R. Geisler
ATTY.

ORNAMENTAL PLUM TREE
Filed May 9, 1955 2 Sheets-Sheet 2
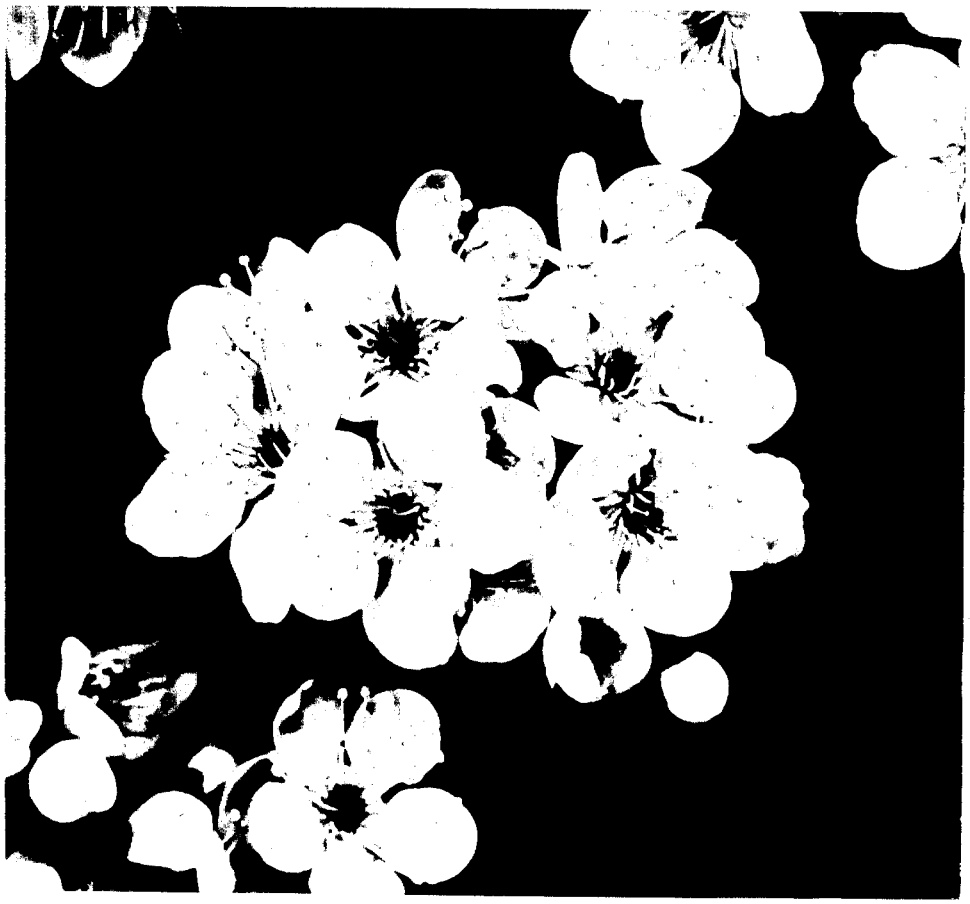

United States Patent Office

Plant Pat. 1,586
Patented Apr. 2, 1957

1,586

ORNAMENTAL PLUM TREE

Mildred M. Smith, Portland, Oreg., assignor to Samuel J. Rich, Hillsboro, Oreg.

Application May 9, 1955, Serial No. 507,192

1 Claim. (Cl. 47—62)

This invention comprises a new and distinct variety of ornamental plum tree, the result of a cross between a Pissardi flowering plum (Prunnus Pissardi) (unpatented) and the Shiro fruit plum (unpatented). The purpose of developing the new variety was to provide a tree which would be highly desirable both as an ornamental tree and as a fruit bearing tree.

The cross pollination was performed under by supervision in April 1947 in the garden of my home on the outskirts of Portland, Oregon, by distributing pollen from a Pissardi flowering plum to blossoms of a Shiro fruit plum. The resulting seed was planted, the seedlings were observed and one seedling, which was considered the most satisfactory was saved. From this seedling other trees were started during the past two years by budding. This reproduction was performed in Hillsboro, Washington County, Oregon. The resulting trees have all been constant and true as regards form, foliage, and fruit.

The accompanying illustrations accurately show a closer view of some of the blossoms on one of the limbs, and a view of the foliage and fruit taken when the fruit was ripe, one of the ripe plums in the last mentioned illustration being cut open to show the color of the flesh of the fruit.

The following is a detailed description of the tree, its blossoms, foliage and fruit.

*Growth and shape of the tree.*—The tree has an open and spreading habit of growth and is of irregular pattern. Its form of growth bears more resemblance to the Shiro than to the Pissardi. It is a very vigorous grower, even more so than the Pissardi.

*Blossoms.*—The blossoms are bluish pink in the bud but become pure white when fully opened and resemble the Pissardi blossom. The stamens are prominent in the blossoms.

*Foliage.*—The leaves, before attaining full growth, are red on both sides, but as they reach their full size they become dark green on the top face and remain red underneath. The color of the top face of the full grown leaves is a deep green, corresponding to color #8 in chart No. 40 of the Cheskin Color Chart (published by Macmillan & Co.). The color on top of the leaves is somewhat darker than the leaves of the Shiro plum tree. On the underside the full grown leaves are wine color, corresponding to color #8 of chart No. 16 of the Cheskin Color Chart. The main rib or vein on the underside is a cherry red of approximately the same color as the fruit and shows up prominently on the underside because of its lighter color.

*Fruit.*—The color of the fruit on the outside is a cherry red, corresponding to color #3 of chart No. 11 of the Cheskin Color Chart. On the inside of the fruit the color of the flesh is apricot-orange, corresponding to color #1 of chart No. 7 of the Cheskin Color Chart. The tree sets fruit as freely as the Shiro plum tree.

The taste of the fruit resembles that of the Shiro, though slightly more acid. It is considerably sweeter than the Pissardi plum. It is slightly smaller than the Shiro plum. The time of the ripening of the fruit is from one week to ten days later than the Shiro plum. After ripening, the fruit remains longer on the tree than the Shiro plum and does not lose any of its flavor upon becoming fully ripe. It also keeps better than the Shiro plum.

Having thus described my invention, I claim:

The new and distinct variety of plum tree as herein disclosed, characterized by its open, vigorous growth, its dark, two-toned foliage, and its cherry red fruit, the foliage and fruit combining to make the tree highly ornamental; the fruit, in addition to its growth, being distinctive by being only slightly acid and being capable of remaining on the tree a considerable time after becoming ripe, while also retaining its full flavor.

No references cited.